United States Patent [19]
Caubere et al.

[11] Patent Number: 5,481,012
[45] Date of Patent: Jan. 2, 1996

[54] PROCESS FOR SELECTIVE EPOXIDATION OF UNSATURATED (METH)ACRYLIC COMPOUNDS AND NEW BIFUNCTIONAL (METH)ACRYLATES OBTAINED

[75] Inventors: Paul Caubere, Nancy; Yves Fort, Vandoeuvre les Nancy; Agnés Ortar, Jarny, all of France

[73] Assignee: Atochem, Paris la Defense, France

[21] Appl. No.: 335,960

[22] Filed: Nov. 3, 1994

Related U.S. Application Data

[63] Continuation of Ser. No. 26,235, Mar. 1, 1993, abandoned, which is a continuation of Ser. No. 630,972, Dec. 21, 1990, abandoned.

[30] Foreign Application Priority Data

Dec. 22, 1989 [FR] France ................. 89/17134

[51] Int. Cl.$^6$ .................. C07D 301/12; C07D 303/16
[52] U.S. Cl. .................. 549/531; 549/553; 549/557; 549/561
[58] Field of Search ................. 549/531

[56] References Cited

U.S. PATENT DOCUMENTS

| | | | |
|---|---|---|---|
| 2,935,516 | 5/1960 | Frostick et al. | 260/348.5 |
| 3,001,975 | 9/1961 | Beaver et al. | 549/561 |
| 3,002,004 | 9/1961 | Beaver et al. | 549/561 |
| 3,459,775 | 8/1969 | Rick et al. | 549/554 |
| 3,992,432 | 11/1976 | Napier et al. | 549/531 |
| 4,359,586 | 11/1982 | Ho et al. | 549/531 |
| 4,954,643 | 9/1990 | Bornengo et al. | 549/531 |
| 5,036,154 | 7/1991 | Au | 549/531 |
| 5,274,140 | 12/1993 | Venturello et al. | 549/531 |

FOREIGN PATENT DOCUMENTS

| | | | |
|---|---|---|---|
| 151941 | 8/1985 | European Pat. Off. | 549/531 |
| 190609 | 8/1986 | European Pat. Off. | |
| 0190609 | 8/1986 | European Pat. Off. | |
| 1206666 | 2/1960 | France | |
| 1205350 | 2/1960 | France | |
| 3602254 | 7/1987 | Germany | 549/531 |
| 156475 | 9/1982 | Japan | 549/531 |
| 56975 | 4/1985 | Japan | 549/531 |
| 991452 | 5/1965 | United Kingdom | |
| 2055821 | 3/1981 | United Kingdom | 549/531 |

OTHER PUBLICATIONS

Chemical Abstracts, vol. 108, No. 16, Apr. 18, 1988, p. 8, 132450e (JP-A-62-81378). (Okamoto).

Chow et al. "Homo-and Copolymers of Vinyl Esters, Acrylates and Methacrylates of Some Derivatives of Fatty Acids," Journal of Applied Polymer Science, vol. 13, pp. 1545–1553 (1969).

Prandi et al, Tetrahydron Letters, vol. 27, No. 23, pp. 2617–2620, 1986.

*Primary Examiner*—Joseph E. Evans
*Attorney, Agent, or Firm*—Millen, White, Zelano, & Branigan

[57] ABSTRACT

Process for the epoxidation of an unsaturated (meth)acrylic compound of formula:

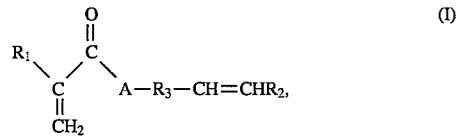

in which $R_1$ is chosen from H and $C_1$-$C_5$-alkyl; $R_2$ is chosen from H, alkyl and aryl; $R_3$ is a straight-chain, branched or cyclic alkylene or oxyalkylene radical having from 1 to 12 carbon atoms, it being possible for one of the carbon atoms of $R_2$, when the latter is an alkyl radical, to be linked to one of the carbon atoms of $R_3$ to form a ring; and A is chosen from O, S, NH and $NR_4$, $R_4$ being a $C_1$-$C_{12}$-alkyl group; by the action of hydrogen peroxide on the said unsaturated (meth)acrylic compound, at a temperature of between 10° C. and 50° C., in the presence of at least one catalyst chosen from the alkali metal molybdates and the alkali metal pertungstates and in the presence of at least one phase transfer agent.

12 Claims, No Drawings

PROCESS FOR SELECTIVE EPOXIDATION OF UNSATURATED (METH)ACRYLIC COMPOUNDS AND NEW BIFUNCTIONAL (METH)ACRYLATES OBTAINED

This application is a continuation of application Ser. No. 08/026,235, filed Mar. 1, 1993, now abandoned, which in turn is a continuation of application Ser. No. 07/630,972, filed Dec. 21, 1990, now abandoned.

The present invention relates to a process for selective epoxidation of unsaturated (meth)acrylic compounds.

The reaction for the epoxidation of unsaturated organic compounds by means of hydrogen peroxide and a salt of a heavy metal acid has been well known for some time. Thus, the U.S. Pat. Nos. 2,833,787 and 2,833,788 describe the epoxidation of non-conjugated ethylenic compounds, for example monoethylenic alcohols, by means of hydrogen peroxide and sodium pertungstate at a pH of between 3 and 7. Similarly, the article published in J. Org. Chem., vol. 24, pages 54–55 (January 1959) describes the epoxidation of $\alpha,\beta$-unsaturated acids by means of hydrogen peroxide and sodium tungstate at a pH of between 4 and 5.5.

The epoxidation of olefins by means of hydrogen peroxide and molybdenum compounds is also disclosed in Angew. Chem. Int. Ed. Engl. 21 (1982) 734–750. Similarly, J. Org. Chem. (1983), Vol. 48, 3831–3833 describes the epoxidation of olefins at 70° C. under phase transfer catalysis conditions by means of dilute hydrogen peroxide (at a concentration of less than 10%) and a water-soluble alkali metal tungstate, at pH 1.6 and in the presence of a phase transfer agent such as a quaternary ammonium or phosphonium halide, the molar ratio of hydrogen peroxide to the olefin being 0.6. The article published by J. Org. Chem. (1985) Vol. 50, 2688–2690 describes a similar reaction carried out at 50° C. in the presence of complexes of molybdenum and monodentate ligands, the molar ratio of hydrogen peroxide to the olefin being 0.2.

Finally, it is known to epoxidise olefins at 60° C. in chloroform, in the presence of a catalyst formed from molybdophosphoric or tungstophosphoric acid and cetylpyridinium chloride, by means of concentrated (35%) hydrogen peroxide and the molar ratio of hydrogen peroxide to the olefin being 1.5 or 1: on this subject reference may be made to J. Org. Chem. (1987), Vol. 52, 1868–1870 and J. Org. Chem. (1988), Vol. 53, 3587–3593.

Moreover, the U.S. Pat. No. 3,459,775 describes the epoxidation of vinylnorbornyl (meth)acrylate at a temperature of 50° C., for a period of 7 to 9 hours, by means of peracetic acid. 2-Epoxyethylbicyclo[2.2.1]hept-5(6)-yl (meth)acrylate is obtained under these conditions in a yield not exceeding 42%. Similarly, the patent application JP-A-62/81 378 describes the epoxidation of dicyclopentenyloxyethyl acrylate at a temperature of 60° C., for 2 hours, by means of hydrogen peroxide at a concentration of 35%. The epoxidised acrylate is obtained under these conditions in a yield not exceeding 48%.

SUMMARY OF THE INVENTION

The problem which the present invention proposes to resolve consists, taking account of the teaching of the prior art recalled above relating to the epoxidation of organic compounds having ethylenic unsaturation, such as olefins, alcohols, acids or some (meth)acrylates, in developing the conditions for the selective epoxidation of non-acrylic unsaturations in unsaturated (meth)acrylic compounds by means of hydrogen peroxide.

In this context, a first subject of the present invention consists of a process for the epoxidation of an unsaturated (meth)acrylic compound of formula:

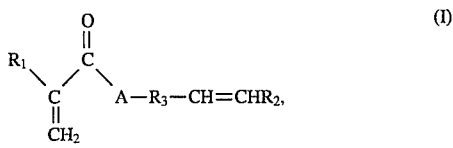

in which:

$R_1$ is chosen from the hydrogen atom and the alkyl radicals having from 1 to 5 carbon atoms, $R_2$ is chosen from the hydrogen atom, the alkyl radicals (in particular those having from 1 to 12 carbon atoms) and the aryl radicals (in particular those having from 6 to 14 carbon atoms), $R_3$ is a straight-chain, branched or cyclic alkylene or oxyalkylene radical having from 1 to 12 carbon atoms, it being possible for one of the carbon atoms of $R_2$, when the latter is an alkyl radical, to be linked to one of the carbon atoms of $R_3$ to form a ring, and A is chosen from the oxygen and sulphur atoms and the radicals NH and $NR_4$, $R_4$ being an alkyl group having from 1 to 12 carbon atoms, by the action of hydrogen peroxide on the said unsaturated (meth)acrylic compound, at a temperature of between 10° C. and 50° C. approximately, in the presence of at least one catalyst chosen from the alkali metal molybdates and the alkali metal tungstates and in the presence of at least one phase transfer agent.

A very large number of unsaturated (meth)acrylic compounds may be epoxidised in accordance with the process according to the invention. They are represented by the above general formula, in which, more precisely:

$R_2$ may be, for example, the hydrogen atom or a methyl, ethyl, n-propyl, isopropyl, n-butyl, iso-butyl, tert-butyl, n-pentyl, n-hexyl, cyclohexyl, n-octyl, n-decyl, n-dodecyl, phenyl, toluyl, xylyl or naphthyl radical, $R_3$ may be, for example, a methylene radical or a polymethylene radical $(CH_2)_n$ with $2 \leq n \leq 12$, an alkylene radical comprising one or more rings, such as the dicyclopentenyl or norbornyl radicals, an oxyalkylene radical $(CH_2)_m$-O-$R_4$ with $1 \leq m \leq 11$ and $R_4$ denoting an alkylene radical which can comprise one or more rings as indicated above, and one of the carbon atoms of $R_2$, when the latter is an alkyl radical, may be linked to one of the carbon atoms of $R_3$ to form a ring.

Preferably, the unsaturated (meth)acrylic compound is stabilised, before reaction, by addition of a compound such as hydroquinone, hydroquinone monomethyl ether, phenothiazine, N,N-diethylhydroxylamine, nitrobenzene, di-tert-butylcatechol, p-anilinophenol, di-(2-ethylhexyl)octylphenyl phosphite and their mixtures in all proportions.

The reaction on which the process according to the invention is based must be carried out at a moderate temperature, avoiding temperatures higher than 50° C. approximately, which are frequently the cause of the polymerisation of the unsaturated (meth)acrylic compound or of its epoxide, and temperatures lower than 10° C. approximately, for reasons of kinetics. The reaction according to the invention is preferably carried out in the presence of a solvent, or of a mixture of organic solvents, which may be chosen, in particular, from the chlorinated solvents, such as dichloroethane, chloroform, carbon tetrachloride, trichloromethane and dichloromethane, and in an amount such that the ratio by volume of compound to be epoxidised/solvent is higher than about 1.5.

The reaction according to the invention is carried out in the presence of one or more phase transfer agents, which may be chosen, in particular, from the family of, for example, quaternary ammoniumhalide salts, such as tricaprylmethylammonium chloride, tetrabutylammonium chloride, tetrabutylammoniumbromide and tetrabutylammonium iodide, or, for example, from the family of quaternary phosphoniumhalide salts, such as tetrabutylphosphonium chloride, tetrabutylphosphonium bromide and tributylhexadecylphosphonium bromide, or may also be tetrabutylammoniumhydrogen sulphate. The phase transfer agent is preferably used in a molar proportion, relative to the compound to be epoxidised, of at least 0.5% and more particularly of between 1% and 3%.

In the process according to the invention, the molar ratio between hydrogen peroxide and the unsaturated (meth)acrylic compound is very important: it is at least one mole, preferably 1.5 to 3 moles, of hydrogen peroxide per mole of unsaturated (meth)acrylic compound. Similarly, the concentration of the hydrogen peroxide, used in aqueous solution, is not without influence on the yield and on the selectivity of the epoxidation reaction: it is preferably between 5% and 50% approximately and more particularly between 10% and 35%. Another important reaction condition is the pH of the mixture: it will preferably be chosen between 1 and 3.5 and more particularly between 1.5 and 2.5, and will be adjusted by means of the necessary amount of an acid such as sulphuric acid and/or phosphoric acid.

Finally, the epoxidation reaction is carried out in the presence of at least one catalyst chosen from the alkali metal molybdates and tungstates of formula $M_2M'O_4$, in which M is an alkali metal chosen from sodium, lithium, potassium, cesium and rubidium and M' is a transition metal chosen from molybdenum and tungsten. This catalyst is preferably used in a molar proportion, relative to the compound to be epoxidised, of at least 0.1% and more particularly of between 0.5% and 5%. The catalyst may also be modified by the addition of an acid, preferably phosphoric acid.

When the unsaturated (meth)acrylic compound is dicyclopentadienyloxyethyl (meth)acrylate or vinylnorbornyl (meth)acrylate, the reaction according to the invention may also be carried out by replacing hydrogen peroxide by an organic per-acid, such as performic acid or peracetic acid, but in this case, without the need for a catalyst and a phase transfer agent, as specified above. In contrast such reactions require the use of stoichiometric amounts of per-acids which make the separation and the purification difficult.

The reaction according to the invention leads, with a degree of conversion which is most often higher than 70%, in a selective manner to the epoxide of formula

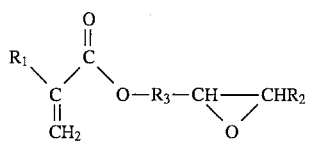

in which $R_1$, $R_2$ and $R_3$ have the abovementioned meanings. The latter is formed preferentially compared to the form of the epoxide of formula:

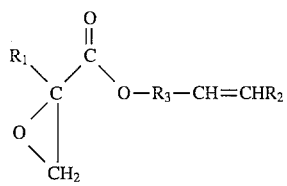

and the corresponding diols, which may constitute byproducts. This result of the invention is particularly surprising to the extent that to date, according to the prior documents already cited, the epoxidation of unsaturated (meth)acrylates proceeded with low yields despite reaction temperatures higher than those specified by the present invention.

Because of their weak odour and their low viscosity, the (meth)acrylates obtained according to the invention could find application as modifiers in the fields of inks, adhesives, paints, coatings and resins.

The following examples are given by way of illustration and do not limit the present invention.

EXAMPLE 1

A solution consisting of 1.5 millimoles of sodium tungstate $Na_2WO_4 \cdot 2H_2O$, 2.55 millimoles of 34% phosphoric acid and 120 millimoles of 20% aqueous hydrogen peroxide, the pH of which has been adjusted to the value indicated in Table I below using a 30% sulphuric acid solution, is added dropwise, in the course of 15 minutes, to a solution consisting of 0.6 millimole of tricaprylmethylammonium chloride (marketed under the name ALIQUAT 336 by Aldrich) and 60 millimoles of allyl methacrylate (marketed by the Applicant) in 15 ml of methylene chloride. The mixture is placed, with vigorous agitation, at the temperature T (expressed in degrees Celsius) indicated in Table I below. A few minutes after the addition, a yellow coloration appears and then fades. The reaction is monitored by gas phase chromatography by analysis of regular samples. At the end of time t (expressed in hours) indicated in Table I below, an acid solution of iron sulphate is added to the reaction mixture in order to destroy the peroxides present in the mixture. At this stage the degree of conversion of the reaction C (expressed in %) and the selectivities S for epoxide of formula (II) (in this case glycidyl methacrylate) and for epoxide of formula (III) indicated in Table I below are calculated.

EXAMPLES 2 AND 3

The method of Example 1 is repeated, except for the following: the aqueous 20% hydrogen peroxide is replaced by aqueous 8% hydrogen peroxide. The other operating conditions and the results of the reaction are collated in Table I.

EXAMPLE 4

The method of Example 1 is repeated, except for the following: the aqueous 20% hydrogen peroxide is replaced by aqueous 35% hydrogen peroxide. The other operating conditions and the results of the reaction are collated in Table I.

EXAMPLE 5

The operating method of Example 1 is repeated, replacing allyl methacrylate by allyl acrylate. The operating conditions and the results of the reaction are collated in Table I. The epoxide of formula (II) formed in this case is glycidyl acrylate.

EXAMPLE 6

The method of Example 1 is repeated, replacing allyl methacrylate by crotyl methacrylate (obtained by transesterification of crotyl alcohol on methyl methacrylate and distilled before use). The operating conditions and the results of the reaction are collated in Table I.

EXAMPLE 7

The method of Example 1 is repeated, replacing allyl methacrylate by decenyl methacrylate (obtained by esterification of dec-9-en-1-ol using methacryloyl chloride). The operating conditions and the results of the reaction are collated in Table I.

EXAMPLE 8

The method of Example 1 is repeated, replacing allyl methacrylate by decyl acrylate (obtained by esterification of dec-9-en-1-ol using acryloyl chloride). The operating conditions and the results of the reaction are collated in Table I.

EXAMPLE 9

The method of Example 1 is repeated, replacing allyl methacrylate by dicyclopentadienyl methacrylate (marketed by the Applicants' assignee). The operating conditions and the results of the reaction are collated in Table I.

EXAMPLE 10

The operating method of Example 1 is repeated, replacing allyl methacrylate by dicyclopentadienyl acrylate. The operating conditions and the results of the reaction are collated in Table I.

EXAMPLE 11

The method of Example 1 is repeated, replacing allyl methacrylate by ethylidenenorbornyl methacrylate (marketed by the Applicants' assignee). The operating conditions and the results of the reaction are collated in Table I.

EXAMPLE 12

The method of Example 1 is repeated, replacing allyl methacrylate by ethylidenenorbornyl acrylate (marketed by the Applicants' assignee). The operating conditions and the results of the reaction are collated in Table I.

EXAMPLE 13

The method of Example 1 is repeated, replacing allyl methacrylate by dicyclopentadienyloxyethyl acrylate (marketed by the Applicants' assignee). The operating conditions and the results of the reaction are collated in Table I.

TABLE I

| Example | pH | T | t | C | S(II) | S(III) |
| --- | --- | --- | --- | --- | --- | --- |
| 1 | 1.9 | 26 | 255 | 90 | 67 | 2.8 |
| 2 | 2.5 | 20 | 96 | 53 | 58 | 6.4 |
| 3 | 3.5 | 20 | 160 | 33 | 74 | 10 |
| 4 | 1.7 | 27 | 160 | 72 | 64 | 4.2 |
| 5 | 2.5 | 25 | 327 | 100 | 70 | 3.5 |
| 6 | 1.7 | 28 | 48 | 87 | 95 | 1.7 |
| 7 | 1.7 | 28 | 29 | 74 | 69 | 2.2 |
| 8 | 1.7 | 28 | 44 | 92 | 94 | 1.4 |
| 9 | 1.7 | 28 | 6 | 95 | 100 | 0 |
| 10 | 1.7 | 30 | 6 | 96 | 100 | 0 |
| 11 | 1.7 | 28 | 5 | 99 | 100 | 0 |

TABLE I-continued

| Example | pH | T | t | C | S(II) | S(III) |
| --- | --- | --- | --- | --- | --- | --- |
| 12 | 1.7 | 28 | 4 | 99 | 100 | 0 |
| 13 | 1.7 | 25 | 18 | 95 | 100 | 0 |

EXAMPLE 14

A solution consisting of 1 millimole of sodium tungstate $Na_2WO_4.2H_2O$, 1.7 millimoles of 34% phosphoric acid and 40 millimoles of aqueous 20% hydrogen peroxide, the pH of which has been adjusted to 1.7 using a 30% sulphuric acid solution, is added dropwise, in the course of 5 minutes, to a solution consisting of 0.4 millimole of tricaprylylmethylammonium chloride and 20 millimoles of cinnamyl methacrylate (obtained by transesterification of cinnamic alcohol on methyl methacrylate and distilled before use) in 10 milliliters of methylene chloride. The mixture is placed, with vigorous agitation, at the temperature T (expressed in degrees Celsius) indicated in Table II below. A few minutes after the addition, a yellow coloration appears and then fades. The reaction is monitored by gas phase chromatography by analysis of regular samples. At the end of the time t (expressed in hours) indicated in Table II below, an acid solution of iron sulphate is added to the reaction mixture in order to destroy the peroxides present in the mixture. At this stage, the degree of conversion of the reaction C (expressed in %) and the selectivities S for epoxide of formula (II) and for epoxide of formula (III) indicated in Table II below are calculated.

EXAMPLE 15

The method of Example 14 is repeated, replacing cinnamyl methacrylate by allyl methacrylate (obtained by esterification of allyl alcohol using methacrylate chloride and distilled before use). The operating conditions and the results are collated in Table II.

EXAMPLE 16

The method of Example 14 is repeated, replacing cinnamyl methacrylate by dicyclopentadienyloxyethyl methacrylate (marketed by the Applicants' assignee). The operating conditions and the results of the reaction are collated in Table II.

EXAMPLE 17

The method of Example 14 is repeated, replacing cinnamyl methacrylate by vinylnorbornyl methacrylate (marketed by the Applicants' assignee). The operating conditions and the results of the reaction are collated in Table II.

EXAMPLE 18

The method of Example 14 is repeated, replacing cinnamyl methacrylate by vinylnorbornyl acrylate. The operating conditions and the results of the reaction are collated in Table II.

EXAMPLE 19

The method of Example 16 is repeated in the absence of 34% phosphoric acid. The operating conditions and the results of the reaction are collated in Table II.

EXAMPLES 20 TO 26

The method of Example 16 is repeated varying the nature of the phase transfer agent which is, respectively, chosen as follows:
tetrabutylammonium chloride (Example 20)
tetrabutylammonium bromide (Example 21)
tetrabutylammonium iodide (Example 22)
tetrabutylammonium hydrogen sulphate (Example 23)
tetrabutylphosphonium bromide (Example 24)
tetrabutylphosphonium chloride (Example 25)
tributylhexadecylphosphonium bromide (Example 26).

The operating conditions and the results of the reaction are collated in Table II.

EXAMPLES 27 AND 28

The method of Example 16 is repeated varying the concentration of aqueous hydrogen peroxide from 8% (Example 27) to 35% (Example 28). The operating conditions and the results of the reaction are collated in Table II.

EXAMPLE 29

The method of Example 16 is repeated, replacing sodium pertungstate by the same molar amount of sodium molybdate $Na_2MoO_4$. The operating conditions and the results of the reaction are collated in Table II.

EXAMPLE 30

The method of Example 16 is repeated, replacing hydrogen peroxide by performic acid produced in situ by the action of aqueous 35% hydrogen peroxide on formic acid in the presence of a few drops of concentrated sulphuric acid. The amounts of the various ingredients are as follows:

| | |
|---|---|
| dicyclopentadienyloxyethyl methacrylate | 0.01 mole |
| formic acid | 0.01 mole |
| 35% hydrogen peroxide | 0.01 mole |
| chloroform (solvent) | 20 ml |

The operating conditions and the results of the reaction are collated in Table II.

EXAMPLE 31

The method of Example 30 is repeated, doubling the amounts of formic acid and hydrogen peroxide (0.02 mole each). The operating conditions and the results of the reaction are collated in Table II.

EXAMPLE 32

The method of Example 31 is repeated, replacing dicyclopentadienyloxyethyl methacrylate by vinylnorbornyl methacrylate. The operating conditions and the results of the reaction are collated in Table II.

EXAMPLE 33

The method of Example 31 is repeated, replacing performic acid by an equivalent amount of peracetic acid. The operating conditions and the results of the reaction are collated in Table II.

TABLE II

| Example | T | t | C | S(II) | S(III) |
|---|---|---|---|---|---|
| 14 | 40 | 49 | 82 | 96 | 1.8 |
| 15 | 38 | 11 | 89 | 90 | 2.4 |
| 16 | 40 | 2.5 | 97 | 100 | 0 |
| 17 | 30 | 22 | 80 | 94 | 0 |
| 18 | 40 | 40 | 81 | 100 | 0 |
| 19 | 40 | 7 | 99.4 | 100 | 0 |
| 20 | 20 | 15 | 96 | 100 | 0 |
| 21 | 20 | 14 | 94 | 100 | 0 |
| 22 | 20 | 15 | 85.5 | 100 | 0 |
| 23 | 20 | 15 | 85.5 | 100 | 0 |
| 24 | 20 | 15 | 98.5 | 100 | 0 |
| 25 | 20 | 15 | 98 | 100 | 0 |
| 26 | 20 | 15 | 95.5 | 100 | 0 |
| 27 | 20 | 2.5 | 91 | 100 | 0 |
| 28 | 20 | 2 | 94 | 100 | 0 |
| 29 | 20 | 234 | 61 | 100 | 0 |
| 30 | 40 | 8 | 92 | 100 | 0 |
| 31 | 40 | 5 | 100 | 95 | 5 |
| 32 | 40 | 22 | 97.5 | 86 | 14 |
| 33 | 40 | 1 | 99.8 | 100 | 0 |

The preceding examples can be repeated with similar success by substituting the generically or specifically described reactants and/or operating conditions of this invention for those used in the preceding examples.

The entire disclosures of all applications, patents, and publications, cited herein, and of corresponding French Application No. 89/17134, filed Dec. 22, 1989, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the selective epoxidation of a non-acrylic ethylenic double bond in an unsaturated (meth) acrylic compound of formula:

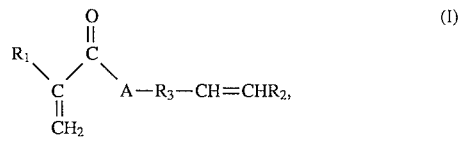

wherein:

R₁ is hydrogen or alkyl having 1–5 carbon atoms;

R₂ is hydrogen, alkyl, or aryl;

R₃ is a straight-chain, branched, or cyclic alkylene or oxyalkylene radical having 1–12 carbon atoms and, optionally, when R₂ is alkyl, one of the carbon atoms thereof may be linked to one of the carbon atoms of R₃ to form a ring; and A is oxygen, sulfur, NH, or NR₄, R₄ being alkyl having 1–12 carbon atoms, comprising reacting hydrogen peroxide with said unsaturated (meth)acrylic compound at a temperature of between 10°–50° C. and a pH of 1.3 to 3.5, in contact with at least one catalyst, said catalyst being an alkali metal molybdate or an alkali metal tungstate, and in the presence of at least one phase transfer agent, wherein the concentration of hydrogen peroxide is 5 to 50%, and the molar ratio between hydrogen peroxide and the unsaturated (meth)acrylic compound is at least 1 mole of peroxide per mole of said compound, and wherein the compound of formula (I) is converted in a selective manner, with a degree of conversion of more than 70% to an epoxide of formula

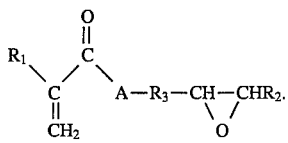
(II)

2. A process according to claim 1, wherein the reaction is carried out in the presence of an organic solvent.

3. A process according to claim 1, wherein the phase transfer agent is a quaternary ammonium or phosphonium salt.

4. A process according to claim 1, wherein the catalyst is used in an amount of at least 0.1 mol % relative to the compound to be epoxidized.

5. A process according to claim 1, where the phase transfer agent is used in an amount of at least 0.5 mol % relative to the compound to be epoxidized.

6. A process according to claim 1, wherein prior to the epoxidation reaction, the compound of formula I is stabilized by the addition of a stabilizing agent selected from the group consisting of hydroquinone, hydroquinone monomethyl ether, phenothiazine, N,N-diethylhydroxylamine, nitrobenzene, di-tert-butylcatechol, p-anilinophenol, di-(2-ethylhexyl)octylphenyl phosphite and mixtures thereof.

7. A process according to claim 1, wherein the phase transfer agent is a quaternary ammonium or phosphonium salt and is present in a molar proportion to the compound to be epoxidized of between 1% and 3%; hydrogen peroxide is employed in a ratio 1.5–3 moles per mole of formula I and at a concentration in aqueous solution of 10–35%; and the pH of the reaction mixture is 1.5–3.

8. A process according to claim 7, wherein prior to the epoxidation reaction, the compound of formula I is stabilized by the addition of a stabilizing agent selected from the group consisting of hydroquinone, hydroquinone monomethyl ether, phenothiazine, N,N-diethylhydroxylamine, nitrobenzene, di-tert-butylcatechol, p-anilinophenol, di-(2-ethylhexyl)octylphenyl phosphite and mixtures thereof.

9. A process according to claim 1, wherein the compound of formula (I) is allyl (meth)acrylate or allyl acrylate.

10. A process according to claim 1, wherein the pH of the reaction mixture has a value between 2.6 and 3.5, inclusive.

11. A process according to claim 1, wherein the pH of the reaction mixture has a value between 1.5 and 3.5, inclusive.

12. A process according to claim 1, wherein $R^1$= H or $CH_3$;

A=O or S;

$R_2$=H, $C_1$-$C_{12}$ alkyl or $C_6$-$C_{14}$ aryl;

$R_3$=straight chain, branched or cyclic alkylene radical having 1–12 carbon atoms and, optionally, when $R_2$ is alkyl, one of the carbon atoms thereof may be linked to one of the carbon atoms of $R_3$ to form a ring.

* * * * *